United States Patent [19]
Padial

[11] Patent Number: 5,890,896
[45] Date of Patent: Apr. 6, 1999

[54] DEVICE FOR THE APPLICATION OF AN IMPRESSION MATERIAL TO THE OCCLUSAL SURFACE OF TEETH

[76] Inventor: Jose Jesus Castro Padial, Lope De Rueda #55, Malaga 29100, Spain

[21] Appl. No.: 815,014

[22] Filed: Mar. 14, 1997

[30] Foreign Application Priority Data

Mar. 15, 1996 [ES] Spain ..................................... 9600654

[51] Int. Cl.$^6$ .................................................. A61C 9/00
[52] U.S. Cl. ............................. 433/40; 433/37; 433/214; 433/215
[58] Field of Search ................ 433/29, 37, 214, 433/229, 215, 71, 40

[56] References Cited

U.S. PATENT DOCUMENTS

| | | | |
|---|---|---|---|
| 1,367,628 | 2/1921 | Roach | 433/40 X |
| 3,357,104 | 12/1967 | Greene et al. | 433/40 X |
| 4,483,675 | 11/1984 | Marshall | 433/40 X |
| 4,522,594 | 6/1985 | Stark et al. | 433/229 |
| 4,553,936 | 11/1985 | Wang | 433/37 |
| 4,615,679 | 10/1986 | Wyatt | 433/229 |
| 4,666,406 | 5/1987 | Kanca, III | 433/229 |
| 4,790,752 | 12/1988 | Cheslak | 433/37 |
| 4,867,682 | 9/1989 | Hammesfahr et al. | 433/37 |
| 4,961,706 | 10/1990 | Jefferies | 433/40 X |
| 5,316,473 | 5/1994 | Hare | 433/29 |
| 5,370,533 | 12/1994 | Bushnell | 433/214 |
| 5,487,662 | 1/1996 | Kipke et al. | 433/37 |

FOREIGN PATENT DOCUMENTS 858006 11/1940 France ..................................... 433/40

*Primary Examiner*—Nicholas D. Lucchesl
*Attorney, Agent, or Firm*—Blank Rome Comisky & McCauley LLP

[57] ABSTRACT

A single tooth handheld dental impression duplicating device and a method of using the device are disclosed. The device is designed to reproduce the occlusal surface anatomy of a particular tooth by making an impression, and after the setting of such material and having obtained the print of the tooth, use the device as a finishing mold for the restorative material. The device comprises a main body (1) with a holder or handle (8) attached to it. Within the main body there is a well defined cavity (3) proximal to the tooth, where the impression material (4) is located. Once the impression material has been softened, it is placed against the occlusal surface of a single tooth and 'deformed' against the tooth surface when finger pressure is applied, thereby creating an impression of the tooth surface configuration. A second cavity (2) opposite to the previously mentioned proximal cavity (3), allows the placement of a fibre optic cable for the emission of light when curing materials are used.

19 Claims, 3 Drawing Sheets

DEVICE FOR THE APPLICATION OF AN IMPRESSION MATERIAL TO THE OCCLUSAL SURFACE OF TEETH

The device of the invention is designed to reproduce the occlusal surface anatomy of a particular tooth by means of an impression, and after the setting of such material and having obtained the print of the tooth, use the device as a finishing mold for the restorative material. The device is composed of a main body (1) with a holder or handle (8) attached to it. Within the main body there is a well defined cavity (3) proximal to the tooth, where the impression material (4) is located. Once the impression material has been softened, it is going to be 'deformed' against the tooth surface when finger pressure is applied, therefore the tooth surface configuration will be obtained, specially the one related to the restorative material (12). A second cavity (2) opposite to the previously mentioned proximal cavity (3), allows the placement of a fibre optic cable for the emission of light when curing materials are used.

OBJECTS OF THE INVENTION

The present invention refers to a device which has been specially conceived, so that an impression material such as silicones, resins, thermoplastics or similar can be applied previous 'recording' of the occlusal surface anatomy of the tooth. On such tooth, once elimination of the damaged areas has been carried out, with the purpose of recovering initial anatomical morphology of the tooth and thus eliminating the usual and time consuming trimming and conventional contouring and finishing of the occlusal surface of the restoration.

BACKGROUND OF THE INVENTION

The conventional techniques carried out by dentists to obtain an adequate occlusal morphology in a particular tooth require the use of burs manufactured in different sizes and materials and in conjunction with rotary instruments, trimming, contouring and polishing are carried out. This is very time consuming and very rarely the operator can reproduce the initial morphology of the tooth accurately, that is, the morphology of the tooth before treatment (cavity preparation) is difficult to be reproduced with precision and some enamel and restorative material can also be accidentally eliminated during the contouring and trimming process.

Elimination of either restorative material or enamel during the contouring and trimming process inevitably leads to the development of incorrect and deficient contact points between the upper and lower teeth. Consequently, overeruption of the opposite tooth may occur and this will cause an occlusal discrepancy which will create discomfort to the patient.

During the trimming and contouring process, some defects may be created at the junction of the restorative material and tooth surface. In these defects, a bacterial population may develop and proliferate more easily and thus failure of the restoration will occur.

The procedures used to repair the damaged occlusal morphology of a tooth are various. For example, prefabricated molds or matrices which simulate a defined standard anatomy and made of different materials can be applied on the tooth. The occlusal anatomy of such tooth, however, can never be accurately reproduced with a non-customized device. The operator is forced to carry out the conventional contouring routine anyway to adapt the mold to each tooth individually. An example of this is the preformed occlusal 'forms' developed for composite fillings or other restorative materials.

An other way to avoid the formation bulges, and bulky edges of restorative material on the margins of the cavity is the 'shaping bite procedure' proposed by Fusayama and described in the Revista Odontoestomatologica Española N° 441, March 1992, page 45, in which the patient actually 'bites' directly onto the still soft restorative material.

Other authors use devices to register the occlusal morphology such as a wooden surface or sheet or similar in conjunction with an opaque impression material. This kind of impression material requires the use of a separating medium to prevent it from adhering to the hardened restorative material. This procedure does not achieve the rigidity and transparency needed for the desired application.

Occlusal conformation systems by mean of complex computers programs (CAD-CAM) reproduce the anatomy of a tooth extrapolating an optic readout before cavity preparation and obtaining a virtual anatomy with great accuracy, manufacturing the final restoration with a robotic cavity preparation system. Even though the fit or adjustment of the final restoration is quite accurate, the occlusal morphology due to the fact that is limited to the use of ceramic materials in a bulk, inserted and cemented in the tooth after its finishing.

The use of impression materials to reproduce the occlusal surface anatomy of teeth is well known by the majority of them are opaque and are taken to the mouth with devices with the shape of an arch (stocks trays) that although rigid, are designed to obtain the mold of the complete dental arch containing teeth and gums, as well as the relationship between upper and lower arches (bit). These trays are often constructed in opaque materials or colored translucid materials (plastic) but the latter can often be subject to deformation when heat is applied to them.

DESCRIPTION OF THE INVENTION

The device that the invention promulgated has been conceived to solve with complete satisfaction the problem and all aspects related to it, allowing the exact reproduction of the occlusal surface anatomy of a particular tooth in an extremely fast and easy way, with no risks of unwanted manipulations.

So that more specifically, the device pictures as a small rigid and transparent body with a handle that makes its use easier, located in this body a formal and dimensional adequate cavity is established prepared to receive in its hollow the occlusal surface and surroundings of a particular tooth, such cavity is destined to carry the impression material that when is applied onto the tooth surface will reproduce the anatomy of such tooth.

The body is made with rigid and stable material which does not deform when exposed to heat and is transparent (translucid) as well. The body incorporates a second cavity or hollow area opposite to the proximal cavity, in which a fibre optic cable can be positioned allowing in conjunction with the transparent nature of the main body, optimal visibly conditions at the working area, that is, at the patient's tooth.

The location in the body for the impression material can be closed in such a way that the amount of impression material can be previously calculated and conveniently placed in the cavity. These may also be an opening, so that after the adjustment of the device on the tooth the impression material can be applied by injection means.

In accordance with another of the characteristics of the invention, the handle or holder will be fixed to the main body with the angulation and orientation that is most adequate depending on the tooth to be treated in each case.

In accordance to what has been previously exposed, the device of the invention can be applied to obtain the occlusal morphology of the tooth or teeth, before caries is cleaned out or eliminated, since in the majority of cases such occlusal morphology remains intact or undamaged as caries extends primarily along the deeper layer of restorative material used such as composite before the latter is set, thus conforming the exact previous morphology of the tooth surface.

It can also be used to register the morphological anatomy of a tooth in a poured cast study laboratory model, previous impression of the arch (with a stock tray) done by the dentist. Teeth that will be prepared by the dentist to receive a crown. This application of the invention involves the taking of the tooth print so that the technician can re-apply the device onto the last layer of wax, resin or ceramic before it hardens so, obtaining the exact previous morphology.

In any case, the object of the invention allows the reproduction of the occlusal surface anatomy of a particular tooth, with no need to register the whole dental arch, saving material and discomfort to the patient, it may also be applied with much precision on the tooth, since is made with a rigid material, with no deformation when pressure to obtain the 'print' is carried out. It allows the flow of light to harden those photosensitive (light curing) materials, as well as at the same time its own transparent nature allows the checking of the correct position of the device on the tooth readily. On the other hand, since the placement of the device involves just the occlusal surface of the tooth and immediate surrounding, isolation of the tooth with rubber dam or similar is advantageous. Rubber dam is a latex film with perforations through which the teeth are inserted and kept isolated from moisture, salivary contamination contraindicated in certain restorative procedures. Moreover, since pressure can readily be applied on the last layer of restorative material to form the print, oxygen is prevented from contaminating the site, which can interfere with the polymerization of certain materials, thus further improving the surface hardness of the restoration.

BRIEF DESCRIPTION OF DRAWINGS

For a more complementary description and to help comprehension of the characteristics of the invention, there is a set of drawings as part of this descriptive account.

PREFERRED EMBODIMENTS OF THE INVENTION

Upon examination of these drawings it can be observed how the device proposed by the invention is composed of a rigid body (1), preferably transparent although it may be translucid in which there are two well defined cavities opposite to each other, a distal cavity (2) opposite to the tooth formed in the upper surface and a proximal cavity formed in the lower surface (3) which is the active part on the tooth and specifically designed to contain an amount of bulk of impression material (4) that previously was placed, or posteriorly injected into place when the device is applied on the tooth. This allows the obtaining of the occlusal anatomy of such tooth before any kind of manipulation takes place as shown in FIG. 1.

Attached to the main body (1) there is a handle appropriately oriented and with a length such the application of such body on the tooth takes place in an easy and comfortable manner.

Figure 1:
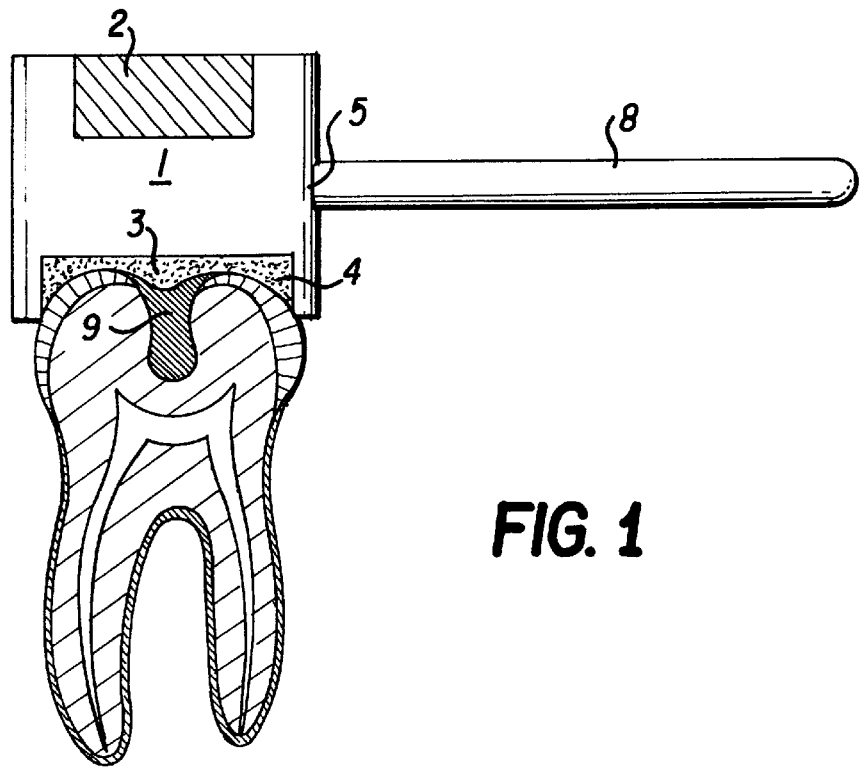
FIG. 1 shows, diagrammatically, a lateral cross sectional view of a device for the application of the impression material to the occlusal surface of teeth, conveniently assembled to a tooth and during the anatomic reproduction phase.
Figure 2:
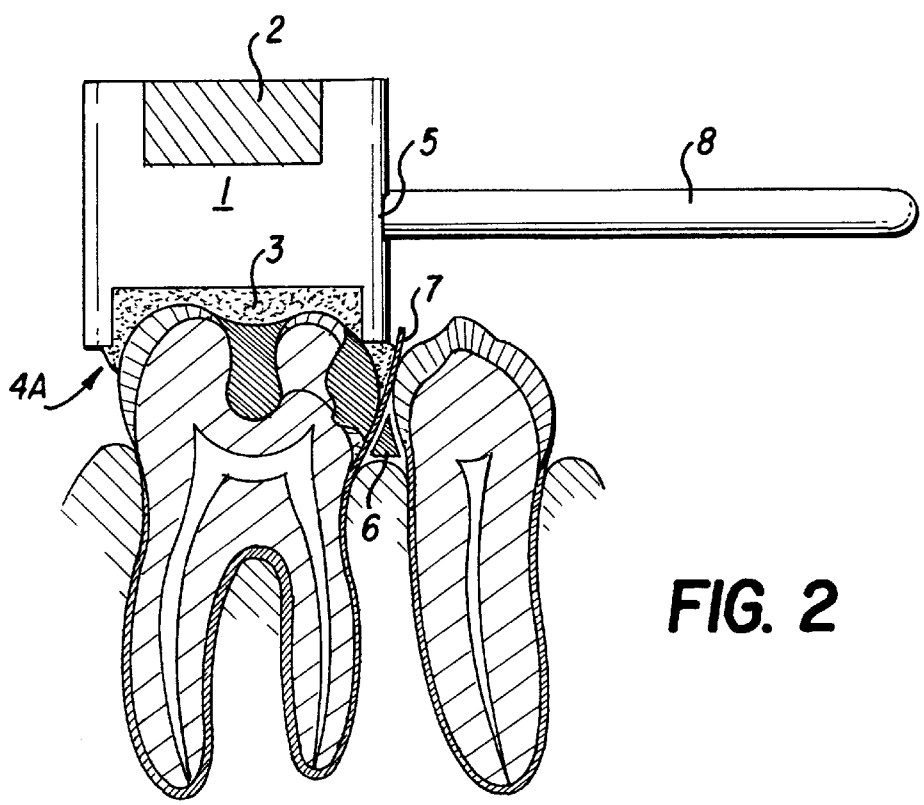
FIG. 2 shows similarly to FIG. 1, the application of the device to a damaged tooth, not only on the occlusal area but also around its immediate surroundings, specifically in its lateral aspect.

Even if the tooth is carious or damaged at its occlusal surface as shown in FIG. 1, where the damaged area is represented as (9), or if the damage extends to the lateral area (interproximal area) as shown in FIG. 2, in which the use of both an interdental wedge (6) and band (matrix) are need, a registration of the anatomy of the tooth by the deformation of the impression material (4) located in the proximal cavity (3) of the device, is readily achieved.

Figure 3:
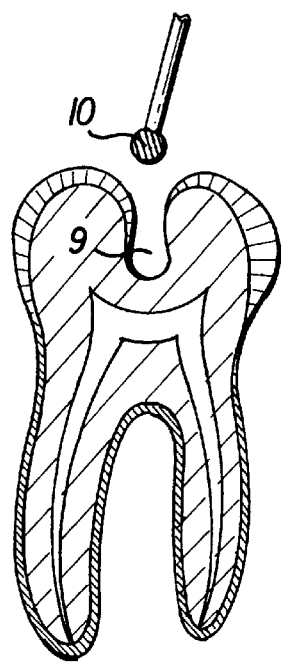
FIG. 3 as shown in FIG. 1 and 2, shows a tooth after the caries elimination phase using a bur or similar tool.
Figure 4:
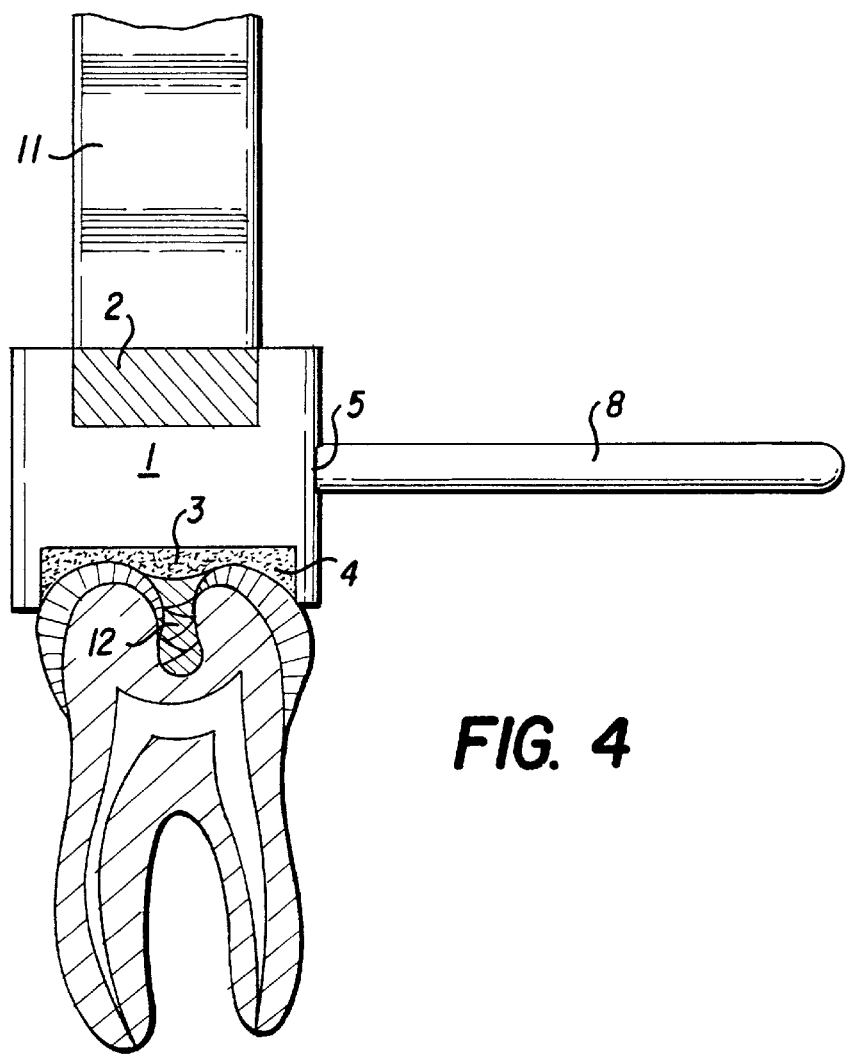
FIG. 4 as shown in FIG. 1, the application of the restorative material and the pressure carried out on the impression material with the device itself.

Once the anatomy is registered, with the use of a bur (10) or similar tool as shown in FIG. 3, the damaged parts (9) of the tooth are eliminated and subsequently a cavity prepared. The restorative material (12) is then placed into the cavity (9) in increments or in bulk if there is conduction connecting the prepared cavity with an injecting system through the already hardened impression material.

In any case, the cavity is adequately filled with the restorative material (composite, resin, wax, porcelain) and with the pressure exerted on the still soft restorative material (12) with the device itself, close fit between device and tooth is obtained adding to this an element of light curing since the distal cavity (2) allows the placement of a cable (11) that emits light directly to the restorative material (12).

Figure 5:
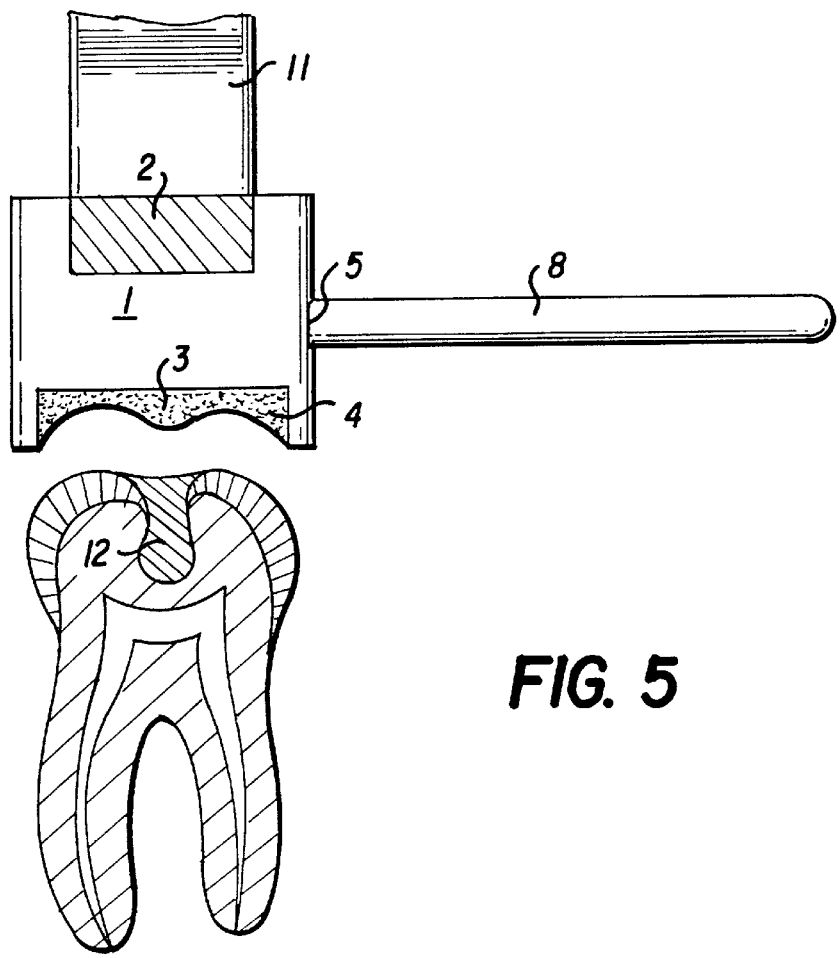
FIG. 5 shows the device detached from the tooth and the latter completely finished.
Figure 6:
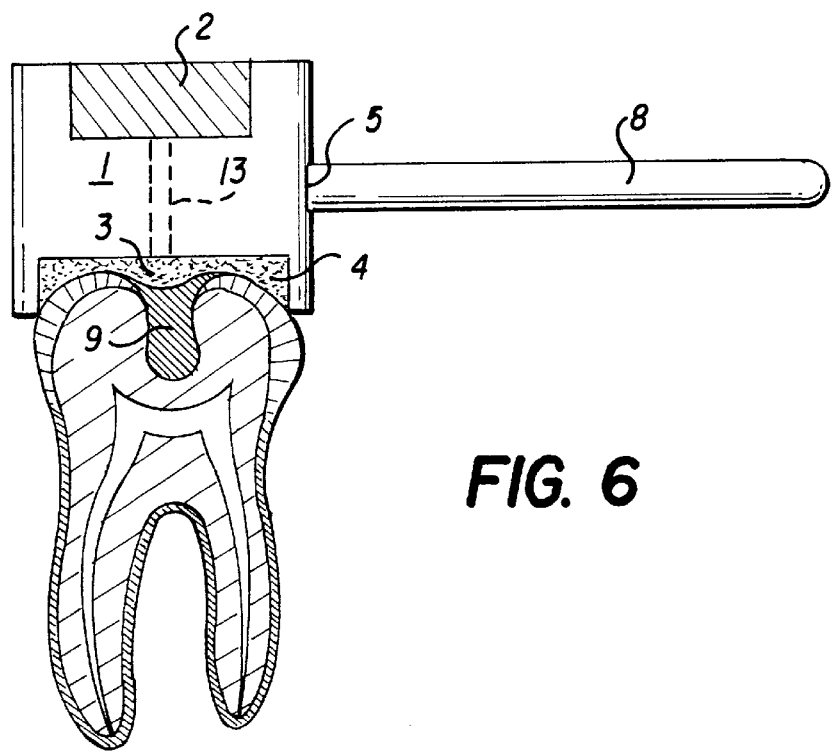
FIG. 6 is an alternate embodiment of FIG. 1 and shows injection of the impression material when the device is applied to the tooth.

Once the restorative material (12) is set and the device is withdrawn as shown in FIG. 5, only a very light surface polishing may be undertaken or carried out if desired. Also, small excess of restorative material at the margins can be eliminated, but these steps will never take as long as the conventional trimming and occlusal contouring usually employed with rotary instruments. As seen in FIG. 6, the device rigid body (1) can alternatively be provided with an orifice (13) which traverses the upper and lower surfaces for receiving impression material (3) by way of an injection device (not shown).

It is considered not to extend this description any further as any expert on the field can fully understand the possibilities of the invention and the advantages derived from it.

The materials, form, shape and disposition of the elements will be subject to variations and changes although these will never alter the essence of the invention.

The terms in which this description has been written should always be taken in a wide general and never in a limited sense. Although certain presently preferred embodiments of the present invention have been specifically described herein, it will be apparent to those skilled in the art to which the invention pertains that variations and modifications of the various embodiments shown and described herein may be made without departing from the spirit and scope of the invention. Accordingly, it is intended that the invention be limited only to the extent required by the appended claims and the applicable rules of law.

What is claimed is:

1. A device for restoring the original occlusal surface anatomy of a single tooth being treated comprising:

a body having upper and lower surfaces, said lower surface being of a size which covers the occlusal surface of a single tooth only and also carries a deformable material for receiving an impression from the occlusal surface to which it is applied, thereby being capable of restoring the original occlusal surface anatomy of said tooth after it is repaired and filled with a restorative material; and said upper surface including receptacle means for receiving a light source.

2. The device of claim 1, further including a handle secured to said body.

3. The device of claim 1, wherein said body is made of an optically transparent material.

4. The device of claim 1, wherein said body lower surface includes receptacle means for receiving said deformable material.

5. The device of claim 4, further including an orifice which communicates with said upper and lower receptacle means, whereby deformable material can be passed therethrough and onto said occlusive surface of said tooth being treated.

6. The device of claim 4, wherein said deformable material is positioned in said lower receptacle means.

7. The device of claim 4, wherein said upper and lower receptacle means are oppositely positioned such that the upper receptacle means is the distal receptacle and the lower surface is the proximal receptacle, and wherein said body is formed of a rigid thermoresistant plastic.

8. The device of claim 1, wherein said light source is a light-transmitting fiber optic cable.

9. A method for restoring the original surface anatomy of a single tooth being treated, comprising the steps:

providing a device having a body with upper and lower surfaces, said lower surface carrying a deformable material for receiving an impression from the occlusal surface of said single tooth being treated;

pressing said deformable material onto the occlusal surface of said tooth to obtain an impression therein and removing said deformable material from said tooth to permit treatment of said tooth;

providing restorative material to said tooth; and exerting pressure on said restorative material using said impression formed in the deformable material carried by said device until said restorative material hardens.

10. The method of claim 9, further comprising curing said restorative material.

11. The method of claim 9, wherein said device further comprises a receptacle in said upper surface of said body for receiving a light source for curing of said restorative material.

12. The method of claim 9, wherein said device of claim 4 is employed.

13. The method of claim 9, wherein said device of claim 5 is employed.

14. The method of claim 9, wherein said device of claim 7 is employed.

15. The method of claim 14, further including the steps of positioning a light transmitting fiber optic cable in said upper receptacle means and hardening said restorative material by transmitting light through said body to said restorative material.

16. A treatment method for applying an impression material to an occlusal surface of a single tooth before treating restorative material, comprising providing a device having a body with a size for treating a single tooth, said body having a lower receptacle;

filling said lower receptacle with a predetermined amount of said impression material;

applying said impression material by means of said device to said occlusal surface of said tooth before any restorative treatment;

curing said impression material to form a mold;

removing caries from said tooth;

incrementally placing restorative material within an empty space in said tooth;

applying said mold to a last layer of said restorative material until said restorative material completely hardens;

coupling a light transmitting fiber optic cable to said device;

curing said restorative material by applying light from said cable; and removing said device from said tooth.

17. The method of claim 16, wherein said device further comprises an upper receptacle in said body opposite said lower receptacle for receiving said fiber optic cable.

18. The method of claim 17, wherein said body is made of a rigid thermoresistant plastic.

19. The method of claim 18, wherein said device includes a handle.

* * * * *